United States Patent [19]

Berg et al.

[11] Patent Number: 5,837,459
[45] Date of Patent: Nov. 17, 1998

[54] NUCLEIC ACID ANALOGUE INDUCED TRANSCRIPTION OF DOUBLE STRANDED DNA

[75] Inventors: Rolf Henrik Berg, Fredericksberg, Denmark; Ole Buchardt, deceased, late of Yaerlose, Denmark, by Dorte Buchardt, heir; Michael Egholm, Lexington, Mass.; Peter Eigil Nielsen, Kokkedal, Denmark

[73] Assignee: Boehringer Mannheim GmbH, Mannheim, Germany

[21] Appl. No.: 653,605

[22] Filed: May 24, 1996

[30] Foreign Application Priority Data

Nov. 25, 1993 [GB] United Kingdom .................. 9324245

[51] Int. Cl.$^6$ .............................. C12Q 1/68; C12P 19/34
[52] U.S. Cl. ......................... 435/6; 435/91.1; 435/91.2; 435/91.21
[58] Field of Search ........................ 530/300; 536/18.7, 536/24.3; 435/91.21, 91.1, 91.2, 6

[56] References Cited

PUBLICATIONS

Daube, et al. 1992, Science, vol. 258 pp. 1320–1324.
Nielsen, et al. 1991, Science, vol. 254, pp. 1497–1500.

*Primary Examiner*—David Guzo
*Attorney, Agent, or Firm*—Nikaido Marmelstein Murray & Oram LLP

[57] ABSTRACT

RNA is transcribed from a double stranded DNA template by forming a complex by hybridizing to the template at a desired transcription initiation site one or more oligonucleic acid analogues of the PNA type capable of forming a transcription initiation site with the DNA and exposing the complex to the action of a DNA dependant RNA polymerase in the presence of nucleoside triphosphates. Equal length transcripts may be obtained by placing a block to transcription downstream from the initiation site or by cutting the template at such a selected location. The initiation site is formed by displacement of one strand of the DNA locally by the PNA hybridization.

59 Claims, 6 Drawing Sheets

E. coli RNA polymerase Run-off transcripts
from PNA loops containing T, G, C and A.

T3 and T7 RNA polymerase transcriptions from a T9C PNA loop

A

A10

B

A10 A10

C

A9GT9CT9C

NUCLEIC ACID ANALOGUE INDUCED TRANSCRIPTION OF DOUBLE STRANDED DNA

CROSS REFERENCE TO RELATED APPLICATION

This application is a continuation-in-part of International Application PCT/EP94/03858, filed Nov. 22, 1994, and designating the U.S.

The present invention relates to the use of analogues of naturally occurring nucleic acids to produce sites for the in vitro initiation of transcription of double stranded DNA, to the production of RNA transcripts thereby, the amplification and/or detection of such transcripts and in vitro diagnostics techniques based on the above.

Analogues of nucleic acids having a peptide or similar backbone bearing pendant ligands such as nucleic acid bases described in WO 92/20703 (PNA's) have been shown to have a number of unusual properties. These include the ability to form complexes with double stranded DNA in which two strands of PNA complementary in sequence to one of the DNA strands hybridise to the DNA displacing the other DNA strand. A high level of sequence specificity has been shown.

Transcription of DNA to form a strand of RNA of corresponding sequence is initiated in nature by the sequence specific recognition of a promotor region of the double stranded DNA either by RNA polymerase or by auxiliary transcription factors. Subsequently, a transcription initiation open complex is formed in which about 12 base pairs of the DNA helix is melted so as to expose the bases of the template strand for base pairing with the RNA strand being synthesised. It has been shown that *E. coli* and phage T7 RNA polymerase can utilise synthetic "RNA/DNA bubble duplex" complexes containing an RNA/DNA duplex and a single stranded DNA D-loop for transcription initiation purposes.

We have now discovered that initiation can similarly be initiated from a strand displacement complex formed between PNA and double stranded DNA. This presents the prospect of having a ready and simple way of preparing single stranded transcripts from a double stranded template.

Generally, techniques for identifying DNA sequences depend upon having the DNA in single stranded form. Once single stranded, the DNA can be hybridised to a probe of complementary sequence and such hybridisation can be detected in various ways. Transcription of RNA from a double stranded template DNA presents an alternative form of method for obtaining a single stranded product for detection and unlike processes of denaturation of the original DNA, it avoids the presence of corresponding amounts of the complementary single stranded product which can compete in the detection process.

Furthermore, the production of an RNA transcript opens the way for amplification of the original DNA sequence without the use of the polymerase chain reaction and without much of the difficulty normally associated with the 3SR amplification technique. In 3SR, a starting RNA is amplified by first hybridising to it a DNA primer constructed to include a T7 polymerase promotor sequence. The primer-DNA/template-RNA is extended in its DNA strand by reverse transcriptase, the RNA strand is digested by RNase H, and the resulting single stranded DNA transcipt is made double stranded with reverse transcriptase to provide a template for transcription by T7 RNA polymerase to make large number of RNA copies. This process is dependent on the construction of a DNA primer of the correct sequence downstream from the T7 promotor sequence. It is further dependent on obtaining the nucleic acid sequense of interest in the form of RNA.

According to the present invention however, a nucleic acid sequence of interest obtained in the form of double stranded DNA can be amplified as multiple single stranded RNA copies by synthesising a primer or multiple primer sequences of the nucleic acid analogue, which will generally be much more straightforward than the prior art methods. The RNA transcripts produced can be converted to DNA if desired.

Accordingly, the present invention provides a method of transcribing RNA from a double stranded DNA template comprising forming a complex by hybridising to said template at a desired transcription initiation site one or more oligo-nucleic acid analogues capable of forming a transcription initiation site with said DNA and exposing said complex to the action of a DNA dependent RNA polymerase in the presence of nucleoside triphosphates.

Optionally, a pair of said oligo-nucleic acid analogues are hybridised to said DNA at spaced locations thereon, on the same or different strands thereof Preferably, said pair of oligo-nucleic acids are spaced by from 0 to 10, more preferably 0 to 5 base pairs of said DNA.

Preferably also, the or each said oligo-nucleic acid analogue has a length of from 5 to 60 nucleic acid analogue units.

Optionally, a block to transcription is placed at a location downstream from said desired initiation site so as to produce equal length transcripts in said transcription. A suitable way of producing a said block is by hybridising to said DNA an oligo-nucleic acid analogue capable of blocking transcription. Otherwise, individual transcription events may terminate randomly downstreams from the initiation site leading to long transcription products of varying length.

The length of the transcripts can also be controlled by cutting the DNA template with a restriction enzyme at a specific downstream location prior to transcription.

The nucleic acid analogue capable of forming a transcription initiation site is preferably a compound that has nucleobases attached to an aminoethylglycine backbone or other like backbone including polyamides, polythioanides, polysulfinamides and polysulfonamides, which compounds we call peptide nucleic acids or PNA. Compounds of this kind surprisingly bind strongly and sequence selectively to both RNA and DNA.

The synthesis of this type of compound is fully described in WO 92/20703.

The recognition by PNA of RNA, ssDNA or dsDNA can take place in sequences at least 5 bases long. A more preferred recognition sequence length is 5–60 base pairs long. Sequences between 10 and 20 bases are of particular interest since this is the range within which unique DNA sequences of prokaryotes and eukaryotes are found. Sequences of 17–18 bases are of special interest since this is the length of unique sequences in the human genome.

Preferably, the or a nucleic acid analogue used is capable of hybridising to a nucleic acid of complementary sequence to form a hybrid which is more stable against denaturation by heat than a hybrid between the conventional deoxyribonucleotide corresponding in sequence to said analogue and said nucleic acid.

Preferably, also the or a nucleic acid analogue used is a peptide nucleic acid in which said backbone is a polyamide backbone, each said ligand being bonded directly or indirectly to an aza nitrogen atom in said backbone, and said ligand bearing nitrogen atoms mainly being separated from one an other in said backbone by from 4 to 8 intervening atoms.

Also, it is preferred that the or a nucleic acid analogue used is capable of hybridising to a double stranded nucleic acid in which one strand has a sequence complementary to said analogue, in such a way as to displace the other strand from said one strand.

More preferred PNA compounds for use in the invention have the formula:

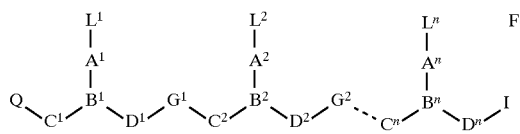

Formula 1 wherein:

n is at least 2, each of $L^1-L^n$ is independently selected from the group consisting of hydrogen, hydroxy, $(C_1-C_4)$alkanoyl, naturally occurring nucleobases, non-naturally occurring nucleobases, aromatic moieties, DNA intercalators, nucleobase-binding groups, heterocyclic moieties, and reporter ligands;

each of $C^1-C^n$ is $(CR^6R^7-)y$ (preferably $CR^6R^7$, $CHR^6CHR^7$ or $CR^6R^7CH_2$) where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$, where $R^3$ and $R^4$ are as defined below, and $R^5$ is hydrogen, $(C_1-C_6)$alkyl, hydroxy, alkoxy, or alkylthio-substituted $(C_1-C_6)$alkyl or $R^6$ and $R^7$ taken together complete an alicyclic or heterocyclic system;

each of $D^1-D^n$ is $(CR^6R^7)_z$ (preferably $CR^6R^7$, $CH_2CR^6R^7$, or $CHR^6CHR^7$) where $R^6$ and $R^7$ are as defined above;

each of y and z is zero or an integer from 1 to 10, the sum y+z being at least 2. preferably greater than 2 but not more than 10, e.g. 3, each of $G^1-G^{n-1}$ is $-NR^3CO-$, $-NR^3C^5-$, $-NR^3SO-$ or $-NR^3SO_2-$, in either orientation, where $R^3$ is as defined below:

each of $A^1-A^n$ and $B^1-B^n$ are selected such that:

(a) A is a group of formula (IIa), (IIb). (IIc) or (IId). and B is N or $R^3N^+$; or (b) A is a group of formula (IId) and B is CH.

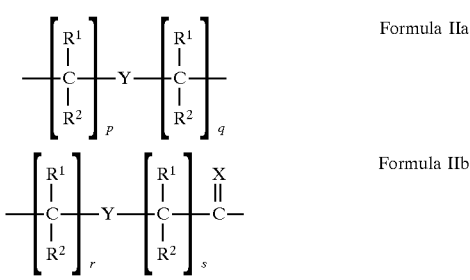

Formula IIa

Formula IIb

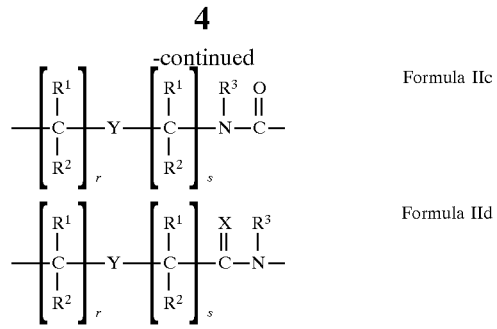

Formula IIc

Formula IId wherein:

X is O.S, Se, $NR^{3,}$ $CH_2$ or $C(CH_3)_2$;

Y is a single bond, O, S or $NR^4$;

each of an q is zero or an integer from 1 to 5, the sum p'q being not more than 10 each of r and s is zero or an integer from 1 to 5, the sum r+s being not more than 10;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and each $R^3$ and $R^4$ is independently selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino;

Q is $-CO_2H$, $-CONR'R''$, $-SO_3H$ or $-SO_2NR'R''$ or an activated derivative of $-CO_2H$ or $-SO_3H$; and I is $NR'''R''''$ or $-NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, including both oligoribonucleotides and oligodoxyribonucleotides, oligonucleosides and soluble and non-soluble polymers. "Oligonucleosides" includes nucleobases bonded to ribose and connected via a backbone other than the normal phosphate backbone of nucleic acids.

In the above structures wherein R', R'', R''' and R'''' are oligonucleotides or oligonucleosides, such structures can be considered chimeric structures between PNA compounds and the oligonucleotide or oligonucleoside.

Generally, at least one of $L^1-L^n$ will be naturally occurring nucleobase, a non-naturally occurring nucleobase, a DNA intercalator, or a nucleobase binding group.

Preferred PNA-containing compounds are compounds of the formula III, IV or V:

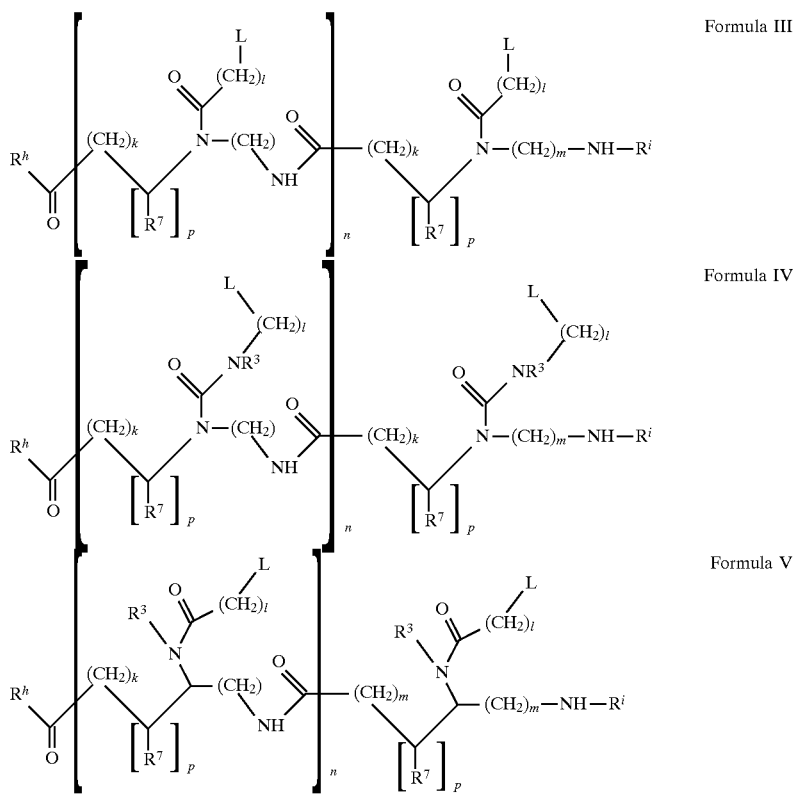

Formula III

Formula IV

Formula V wherein:

each L is independently selected from the group consisting of hydrogen, phenyl, heterocyclic moieties, naturally occurring nucleobases, and non-naturally occurring nucleobases;

each $R^7$ is independently selected from the group consisting of hydrogen and the side chains of naturally occurring alpha amio acids;

n is an integer greater than 1, each k, l, and m is, independently, zero or an integer from 1 to 5;

each p is zero or 1;

$R^h$ is OH, $NH_2$ or —$NHLysNH_2$; and $R^1$ is H or $COCH_3$.

The invention includes a diagnostics method comprising carrying out a transcription to produce RNA in accordance with the methods of the invention as described above and detecting the production of said RNA. Such a method may be used to test for the presence or absence in sample DNA of a sequence matching that of one or more PNA's employed.

Suitable, said RNA is captured to a nucleic acid probe of complementary sequence and is also bound to a nucleic acid probe bearing a detectable label.

The invention includes a method of nucleic acid amplification comprising preparing an RNA transcript from DNA by a method in accordance with the above description and in such a way as to produce multiple RNA transcript copies from each molecule of DNA template.

If desired RNA transcribed according to the invention can be further amplified using the 3SR technique.

A further subject of the invention is a method of converting a (starting) nucleic acid into a substrate for transcribing RNA including forming a counterstrand of said nucleic acid incorporating a specific binding sequence, hybridizing the nucleic acid with a nucleic acid analogue, preferably a peptide nucleic acid, complementary to the specific binding sequence, and treating the mixture under conditions adapted for transcription under the control of the newly created promotor side.

In a specific embodiment (described with reference to FIG. 6) an RNA to be transcribed is hybridized to a DNA-oligonucleotide containing at least one nucleic acid sequence S1 hybridizable with said RNA in the region of the 3'-end of said RNA. This sequence may have a length of at least 15 nucleotides, preferably of about 20 nucleotides. Especially preferred the oligonucleotide contains an additional nucleotide sequence S2 which can hybridize to a site which is located even more at the 3'-end of the RNA. This sequence may be more than 15 nucleotides long, but will preferably be about 40 nucleotides long. In this preferred embodiment the 2 sequences of the oligonucleotide are connected to each other by a third sequence S3 which will be the specific binding sequence, adapted in sequence for specific hybridization to a nucleic acid analogue used as the promotor initiation site. Therefore the third sequence is preferably more than 8 nucleotides long preferably about 10 nucleotides. These nucleotides preferably contain only pyrimidine bases as nucleobases. Especially preferred the third sequence consists of a homopyrimidine stretch.

The sequences of the starting RNA which correspond to the first and second sequence of the oligonucleotide are separated from each other by a sequence of about the same length as the third sequence, but not being able to hybridize to the third sequence.

For the incorporation of the specific binding sequence (third sequence) the oligonucleotide is hybridized to the nucleic acid and extended by additional mononucleotides using the starting RNA as a template. This is made by the reverse transcriptase reaction which is known in the art. This will leed to a partially double stranded nucleic acid, which contains a stretch being able to hybridize with a sequence complementary to the specific binding sequence. In a further step, this hybrid is brought into contact with the nucleic acid analogue to hybridize with said specific binding sequence. In case of a homopyrimidine stretch the nucleic acid analogue will contain the corresponding homopurine stretch.

According to the invention this construct will act as a substrate for an RNA polymerase for the production of RNA in a transcription reaction. This simple hybridization and elongation reaction provides simple access to RNAs, especially when introduced into an amplification cycle like NASBA or 3SR.

In another embodiment (described with reference to FIG. 7) a single DNA is used to produce the above mentioned double stranded nucleic acid containing the specific stretch. In this embodiment the single stranded DNA is hybridized to a DNA-oligonucleotide as described with reference to FIG. 1. Then reverse transcriptase or DNA dependent DNA polymerase is added to extend this oligonucleotide using the DNA as a matrix. After denaturation a primer complementary to the extension product is added and elongated to produce an extension product complementary to the first extension product. Then the nucleic acid analogue is added and transcription is initiated.

The invention will be further illustrated by the following examples which make reference to the appended drawings in which.

EXAMPLE 1

Transcription Initiation (1) by single oligo-PNA, (2) by two oligo-PNA's Arranged trans and (3) by two oligo-PNA's Arranged cis.

Restriction fragments of three plasmids pT9C, pT9CT9C (pUC19 derivatives containing respectively the sequences T9C and T9CT9C) and pT9CA9GKS (Bluescript KS+derivative containing a T9CA9G sequence) were isolated by digestion with PvuII and purification on polyacrylamide gels resulting in fragments of 338 base pairs (pT9C), 354 base pairs (pT9CT9C) and 477 base pairs (pT9CA9GKS). PNA-DNA complexes were formed by incubating PNA with the DNA fragments in 10 mM Tris-HCl pH 8.0 and 0.1 mM EDTA in total volume of 15 µl for 1 hour at 37° C. The reaction mixture was adjusted to contain a final concentration of 40 mM Tris-HCl pH 7.9, 120 mM KCl, 5 mM $MgCl_2$, 9.1 mM DTT, and 1 mM of ATP, CTP, GTP and 0.1 mM of UTP and 5 $\mu Ci^{32}P$ UTP. The PNA used was T9C-lysNH$_2$ in each case.

The transcriptions were initiated by addition of 100 nM E Coli RNA polymerase holoenzyme (Boehringer Mannheim GmbH). The mixtures (total volume of 30 µl) were incubated at 37° C. for 20 minutes and the RNA produced by transcription was subsequently recovered by ethanol precipitation. The RNA transcripts were analysed on 8% denaturing polyacrylamide gels, and visualised by autoradiography to produce the gel shown in FIG. 1.

Figure 1:
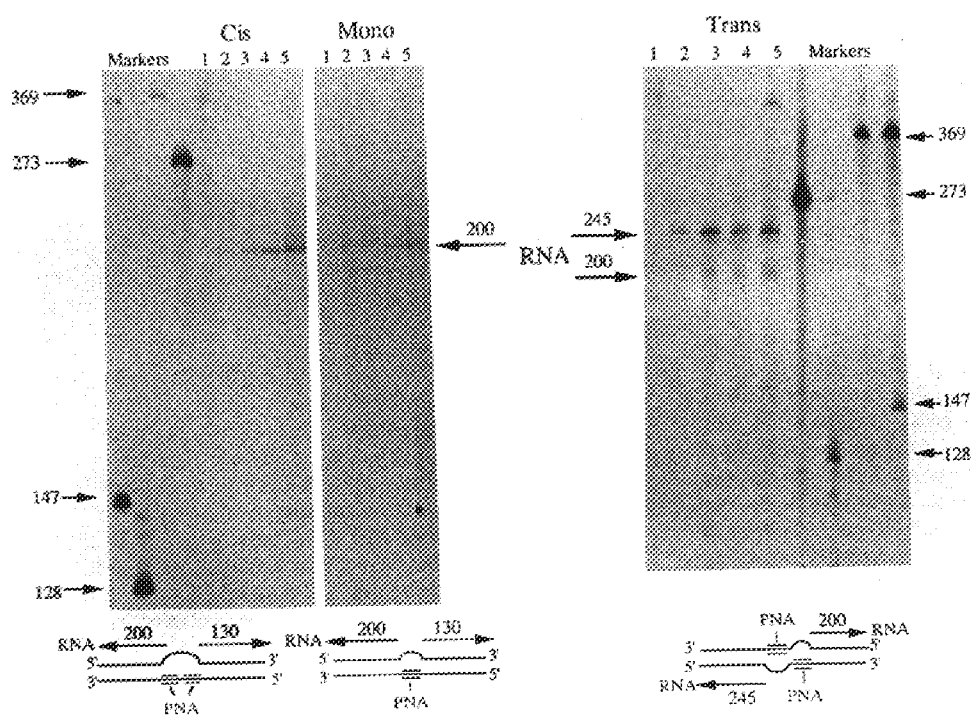
FIG. 1 is an autoradiograph of a gel produced in Example 1.

As shown in the schematics in FIG. 1, the three plasmids used provide respectively a single binding site for the PNA (mono), a pair of binding sites on the same DNA strand (cis), and a pair of binding sites on opposite strands of the DNA (trans).

The lanes of the gel show the effect of varying concentrations of PNA as follows:

Lanes 1, 6 and 11: 0M
Lanes 2, 7 and 12: 3 nM
Lanes 3, 8 and 13: 10 nM
Lanes 4, 9 and 14: 3 µm
Lanes 5, 10 and 15: 10 µm The plasmids used in the lanes were as follows:
Lanes 1–5: pT9C
Lanes 6–10: pT9CT9C
Lanes 7–15: pT9CA9G Lane 5 shows the production of a single RNA product having the size expected if transcription proceeds from the PNA binding site in the direction shown in the corresponding schematic.

Lane 10 similarly shows the production of one RNA transcript but transcription is shown to be more efficiently promoted by the presence of two oligo PNA's at the binding site arranged in cis.

Lanes 13 to 15 show the production of two transcripts of the sizes expected if transcription is initiated on each of the two DNA strands and proceeds from the respective binding site to the end of the DNA fragment as illustrated in the schematic.

It is estimated that in those lanes were transcript RNA is seen, from 1 to 5 RNA molecules are being produced per DNA template molecule during the 20 minute incubation with RNA polymerase.

EXAMPLE 2

Transcription Initiation by Single PNA Oligomers of Varying Base Sequence

Figure 2:
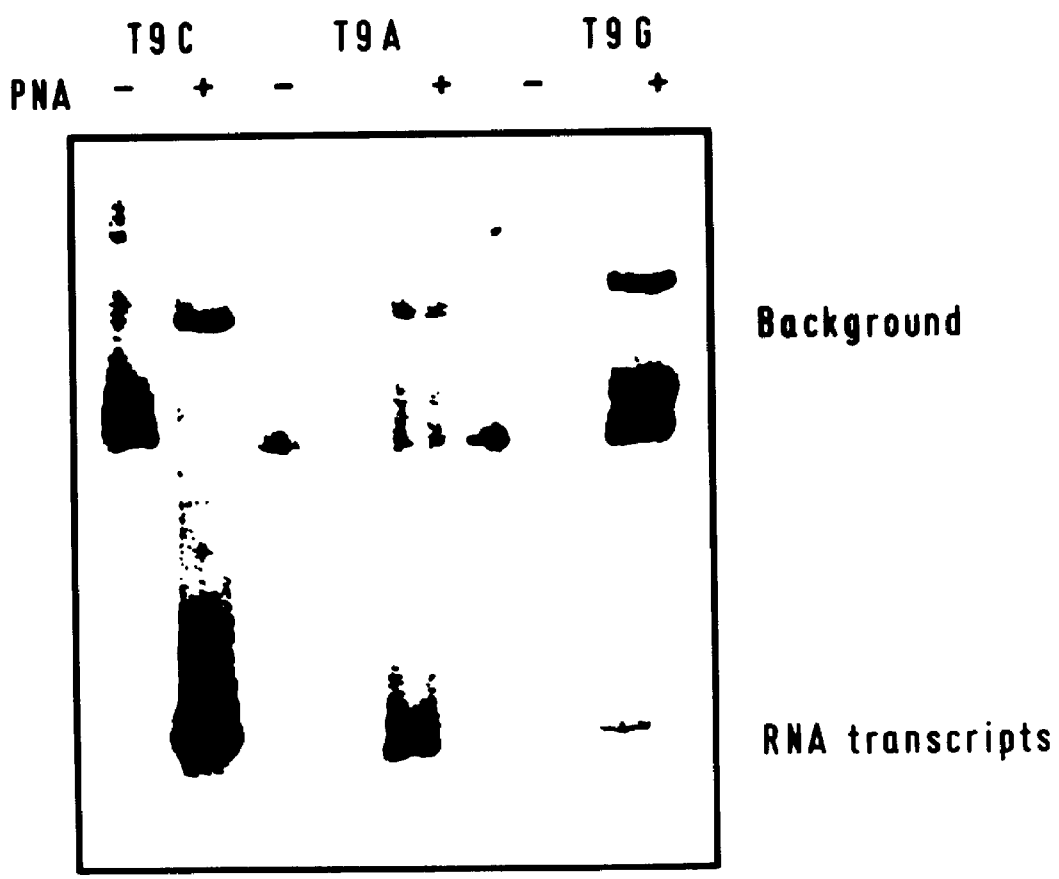
FIG. 2 is an autoradiograph of a gel produced in Example 2.

Restriction fragments o f plasmids containing the sequences T9C, T9A, an d T9G were isolated. PNA-DNA complexes were formed with PNA oligomers of corresponding sequence as described in Example 1 and transcription was initiated also as described in Example 1 using E. coli polymerase. The resulting transcripts were visualized by autoradiography to produce the autoradiography shown in FIG. 2, demonstrating that transcription is obtainable whichever of the bases A, C and G is present. Lanes 1, 3 and 5 are control lanes run without PNA present during the attempted transcription.

EXAMPLE 3

Transcription Initiation by Single PNA Oligomers using T7 and T3 Polyermase

Figure 3:
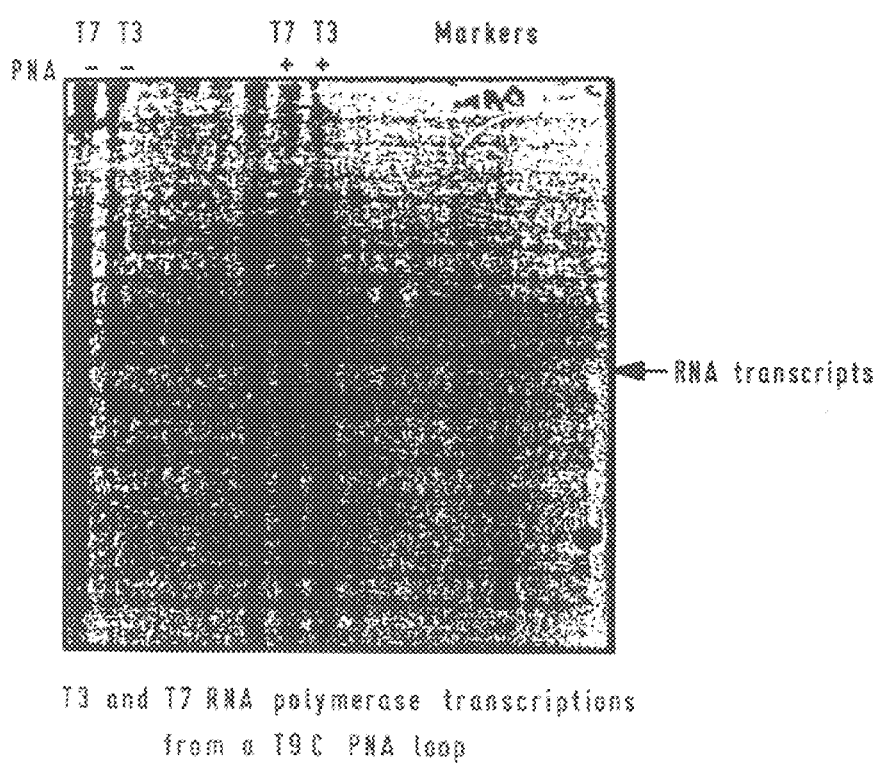
FIG. 3 is an autoradiograph of a gel produced in Example 3.

Using the restriction fragment from the plasmid pT9C and the PNA oligomer T9C described in Example 1, transcription was initiated generally as described in Example 1 but using separately T3 and T7 polymerase to produce the autoradiograph shown in FIG. 3. Lanes 1 and 2 are controls run in the absence of PNA during attempted transcription with T7 (lane 1) and T3 (lande 2) and lanes 5 and 6 show the effect of the presence of PNA T9C on transcription mediated by T7 (lane 5) and T3 (lane 6).

EXAMPLE 4

Figure 4:
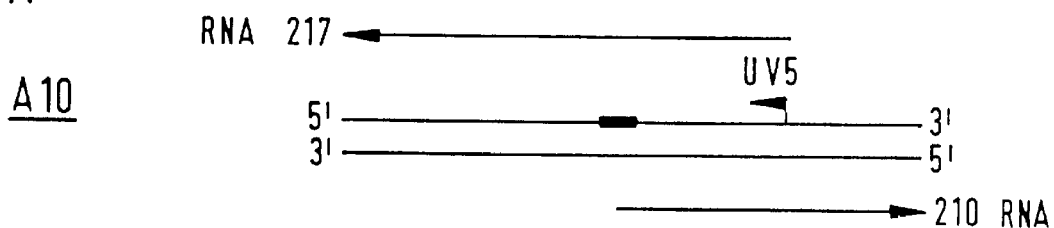
FIG. 4 is a model figure showing construction of the different PNA promotors used in the experiments of FIG. 5.
Figure 4:
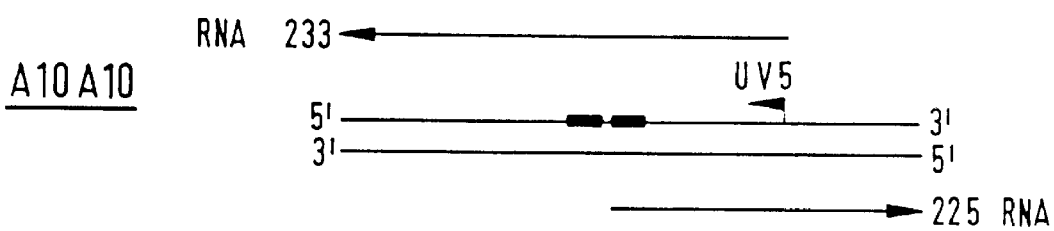
Figure 4:
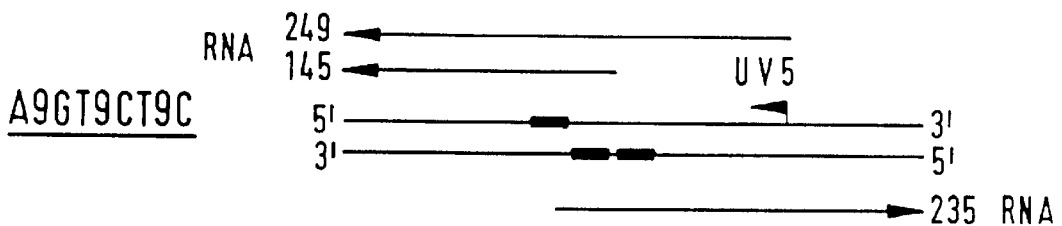

Transcription Initiation using a Second PNA Oligomer Hybridizing Downstream from the First Transcription Initiation Site Experiments were undertaken to estimate the strength of the PNA-dependent transcription initiation. This was done by having both the strong lacUV5 E. coi promotor and one or more PNA targets on the same DNA fragment. These constructs and the results of the transcription experiments are presented in FIGS. 4 and 5. With the constructs containing one or two PNA $T_{10}$ targets on the template strand downstream form the lacUV5 promotor (FIG. 4A and B) two new transcripts are observed as the PNA concentration is increased. One transcript is assigned to be initiated at the PNA target, while the other is assigned to be initiated from the UV5 promotor and arrested at the PNA site. A construct having two PNA T4CT5 targets on the template strand and one on the non-template strand only produced transcripts assigned to be initiated at the two PNA loops and proceeding in opposite directions. The intensity of the RNA bands decreased at higher PNA concentrations, most likely as a consequence of full occupancy of all PNA sites, since an occupied PNA site downstream form the PNA loop would arrest synthesis from this loop. It is also observed that the intensity of the band corresponding to transcription from the larger loop is significantly more intensive than that of the transcription from the smaller loop, indicating a more efficient transcription from the larger loop. This difference is more pronounced than is apparent from the autoradiograph taking into account the different sizes of the transcripts.

Figure 5:
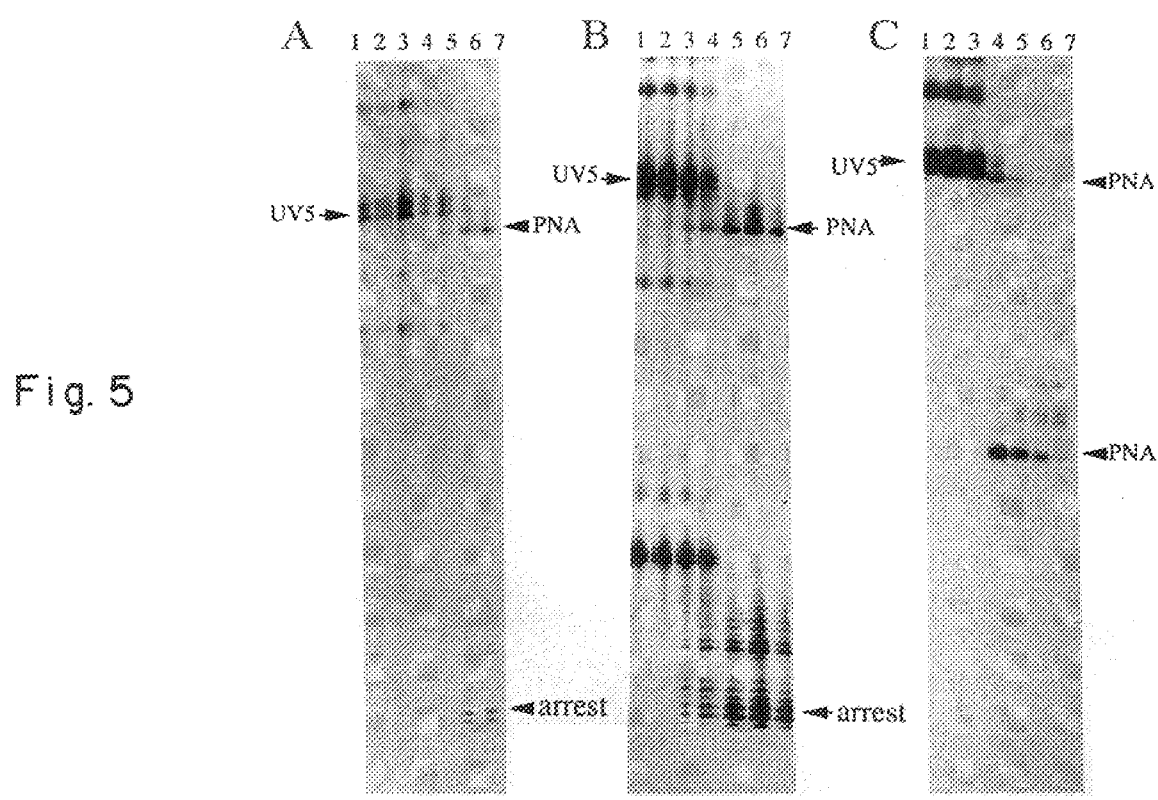
FIG. 5 is an autoradiograph of an experiment showing competition between PNA promotors and the lacUV5 promotors.
Figure 6:
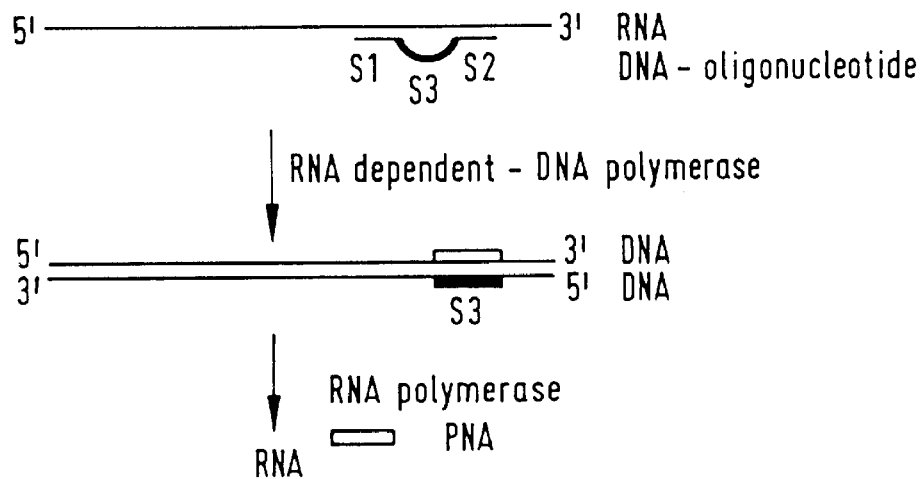
FIG. 6 and 7 show schemes for preferred embodiments of the invention.
Figure 7:
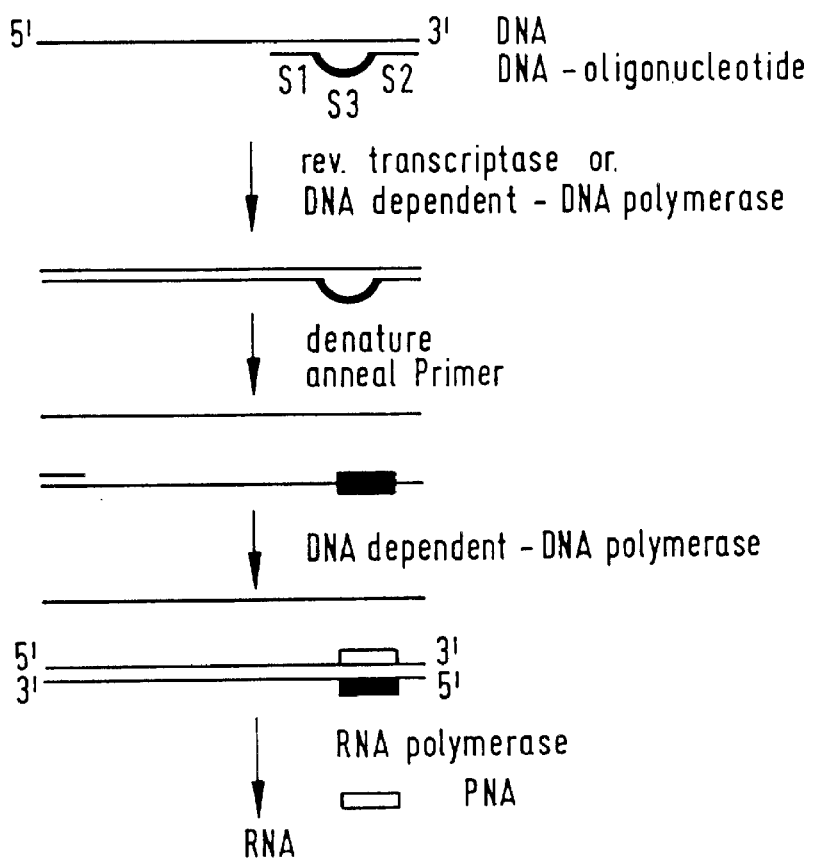

The relative positions of hybridization are shown in FIG. 5. The sequence to the left indicates the PNA targets corresponding to the upper strand from 5' to 3' in the models. PNA binding is shown by thick bars. The direction of transcription is shown with the approximated length of the RNA product indicated.

The fragment including a single, a double, or a triple PNA binding site together with the lacUV5 promotor was incubated with the desired amount of PNA for 1 hr at 37° C. The transcription reactions were performed as described above except that 20 nM E. coli RNA polymerase was used.

The plasmids pT9C, pT9CT9C (pUCI9 derivatives), pT9CA9GKS, pT10KS, and pA10KS (Bluescript KS+derivatives) were constructed as described Nielsen, P. E., Egholm, M., Berg, R. H. & Buchardt, O. (1993) Anti-Cancer Drug Des. 8, 53–63; Nielson, P. E. Egholm, M., Berg, R. H. & Buchardt, O. (1993) Nucleic Acids Res. 21, 197–200. The plasmid pUV5 was constructed by cloning a 203-bp Eco RI fragment containing the lacUV5 promotor (position -150 to +93) into the Eco RI site of pUC18. pT9C-UV5 contains three PNA $T_4CT_5$ targets each separated by 6bp. pA10UV5 contains a single PNA $T_{10}$ target cloned in the BamHI site of pUV5 ($A_{10}$ on the template strand), while pA10A10UV5 contains two $T_{10}$ PNA targets separated by a 6-bp linker cloned in the BamHI site of pUV5 (both $A_{10}$ on the template strand). The PNA was synthesized as described (Egholm, M., Buchardt, O., Nielsen, P. E. & Berg, R. H. (1992) J. Am. Chem. Soc. 114, 1895–1897, Egholm, M., Buchardt. O., Nielsen, P. E. & Berg, R. H. (1992) J. Am. Chem. Soc. 114, 9677–9678).

Restriction fragments of the plasmids were isolated by digestion with Pvu II and purification on low-melting agarose gels resulting in fragments of 338 bp (pT9C), 354 bp (pT9CT9C), 461 bp (pA10KS and pT10KS), 477 bp (pT9CA9GKS), 354 bp (pA10UV5), 370 bp (pA10A10UV5), or 386 bp (pT9CUV5).

In vitro transcription from purified DNA fragments containing a single PNA $T_{10}$ target (pA10UV5) (A), two PNA $T_{10}$ targets in cis (pA10A10TV5) (B) or a triple PNA T??$CT_4$ target (one in trans and two in cis) (pT9CUV5) (C) as well as a lacUV5 promotor. The concentrations of PNA were as follows: lanes 1, 0 nM, lanes 2, 1 nM, lanes 3, 3 nM, lanes 4, 10 nM, lanes 5, 30 nM, lanes 6, 0.1 μM, lanes 7, 0.3 μM. Seventy nanomolar DNA was used in all experiments. Transcription from the UV5 and the PNA promotors are marked with arrows as is transcription arrest.

The experiments clearly show that the transcription initiated at the first initiation site (UV5) is stopped at the second site, allowing the production of RNA of defined length. In addition to that, the second site acts as an initiator for transcription starting at the second site.

In the above description, alkyl moieties, unless otherwise specified, preferably contain 1–6, most preferred 1–3 carbon atoms. Aromatic moieties, preferably 6–14, most preferred 6–10 carbon atoms. Both alkyl moieties and aromatic moieties may be substituted or unsubstituted by groups containing heteroatoms, such as O, N or S. The alkyl moieties can be straight-chained or branched.

Preferred aromatic moieties are phenyl, imidazolyl, or pyridyl. Preferred DNA intercalators include anthraquinolyl, psoralyl or ethidium bromide.

Preferred heterocyclic moieties include piperidinyl, morpholinyl or pyrrolidinyl.

Preferred reporter ligands include biotinoyl, dioxigenoyl or fluoresceinoyl.

Preferred chealting moieties include EDTA, NTA or bispyridinoyl.

Preferred aryl groups are phenyl. Preferred aralkyl groups are tolyl. Preferred heteroaryl groups include pyrimidinyl.

Preferred alicyclic or heterocyclic groups for $R^6$ and $R^7$ include cyclohexenoyl and piperazinoyl.

Examples of groups for R', R", R''' and R'''' are the following:

alkyl: methyl; an amino protecting group: t-butyloxycarbonyl; a reporter ligand: biotin; an intercalator: anthraquinolyl; a chelator: bispyridyl; a peptide: kemptide; a protein: alkaline phosphatase; a carbohydrate: sucrose; a lipid: cholesterol; a steroid: dioxigenin; a nucleoside: adenosin; a nucleotide: adenosine monophosphate; a nucleotide diphosphate: adenosine diphosphate; a nucleotide triphosphate: adenosine triphosphate; an oligonucleotide: $A^{10}$; a soluable polymer: dextrane; a non-soluable polymer: magnetic bead.

We claim:

1. A method of transcribing RNA, using a double-stranded DNA as a template, comprising:
    (a) hybridizing said double-stranded DNA with a least one oligo-nucleic acid analogue to form a hybrid having a transcription initiation site, wherein the hybrid is more stable against heat denaturation than a hybrid between a conventional deoxyribonucleotide corresponding in sequence to said at least one oligo-nucleic acid analogue;
    (b) combining said hybrid with a prokaryotic DNA dependent RNA polymerase and a plurality of nucleoside triphosphates; and
    (c) thereafter transcribing said RNA by attaching together a plurality of nucleoside triphosphates from step (b), using said double-stranded DNA as a template.

2. The method according to claim 1, wherein said at least one oligo-nucleic acid analogue comprises 5 to 60 base pairs.

3. The method according to claim 1, wherein said at least one oligo-nucleic acid analogue comprises 10 to 20 base pairs.

4. The method according to claim 1, wherein said at least one oligo-nucleic acid analogue comprises 17 to 18 base pairs.

5. The method according to claim 1, wherein said at least one oligo-nucleic acid analogue is a peptide nucleic acid.

6. The method according to claim 1, wherein said at least one oligo-nucleic acid analogue comprises a plurality of nucleotide bases attached to a backbone, said backbone comprising a polymer selected from the group consisting of polyaminoethylglycine, polyamide, polythioamide, polysulfinamide and polysulfonamide.

7. The method according to claim 1, wherein said at least one oligo-nucleic acid analogue comprises a polyamide backbone and a plurality of ligands, each of said plurality of ligands being bonded directly or indirectly to an aza nitrogen atom in said polyamide backbone, wherein a plurality of the ligands bear at least one nitrogen atom and each of said plurality of ligands which bears at least one nitrogen atom is separated from another of said plurality of ligands which bears at least one nitrogen atom by from 4 to 8 intervening atoms in said polyamide backbone.

8. The method according to claim 1, wherein said at least one oligo-nucleic acid analogue hybridizes with one strand of said double-stranded DNA having a sequence which is complementary to said at least one oligo-nucleic acid analogue, thereby displacing the other strand of said double-stranded DNA from said one strand of said double-stranded DNA.

9. The method according to claim 1, wherein said at least one oligo-nucleic acid analogue is a compound of formula 1:

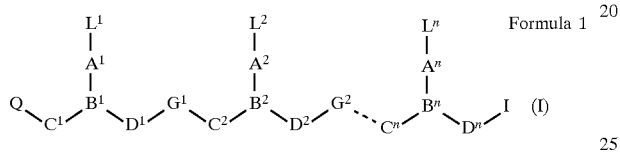

wherein:
n is at least 2,
each of $L^1$–$L^n$ is independently selected from the group consisting of hydrogen, hydroxy, ($C_1$–$C_4$)alkanoyl, a naturally occurring nucleobase, a non-naturally occurring nucleobase, an aromatic moiety, a DNA intercalator, a nucleobase-binding group, a heterocyclic moiety, and a reporter ligand;
each of $C^1$–$C^n$ is independently selected from the group consisting of $(CR^6R^7)_y$, $(CHR^6CHR^7)_y$ and $(CR^6R^7CH_2)_y$
wherein $R^6$ is hydrogen and $R^7$ is selected from the group consisting of one of the side chains of naturally occurring alpha amino acids, or
$R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$) alkylthio, $NR^3R^4$ and $SR^5$, wherein $R^3$ and $R^4$ are as defined below, and wherein $R^5$ is selected from the group consisting of hydrogen, ($C_1$–$C_6$)alkyl, hydroxy, alkoxy and alkylthio-substituted ($C_1$–$C_6$) alkyl, or
$R^6$ and $R^7$, taken together, form an alicyclic or heterocyclic system;
each of $D^1$–$D^n$ is independently selected from the group consisting of $(CR^6R^7)_z$, $(CH_2CR^6R^7)_z$ and $(CHR^6CHR^7)_z$
wherein $R^6$ and $R^7$ are as defined above;
each of y and z is zero or an integer from 1 to 10, y+z being at least 2;
each of $G^1$–$G^{n-1}$ is independently selected from the group consisting of —$NR^3CO$—, —$CONR^3$—, —$NR^3CS$—, —$CSNR^3$—, —$NR^3SO$—, —$SONR^3$—, —$NR^3SO_2$— and —$SO_2NR^3$—, where $R^3$ is as defined below;
each of $A^1$–$A^n$ and $B^1$–$B^n$ are selected such that:
(a) A is selected from the group consisting of a group of formula (IIa), (IIb), (IIc) and (IId), and B is N or $R^3N^+$, or (b) A is a group of formula (IId) and B is CH;

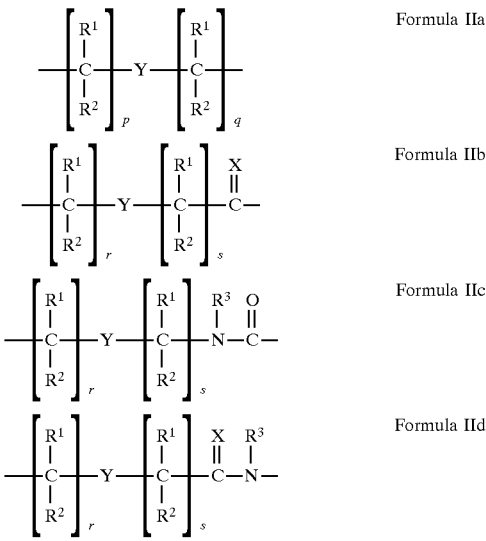

wherein:
X is selected from the group consisting of O, S, Se, $NR^3$, $CH_2$ and $C(CH_3)_2$;
Y is selected from the group consisting of a single bond, O, S and $NR^4$;
each of p and q is zero or an integer from 1 to 5;
each of r and s is zero or an integer from 1 to 5;
each of $R^1$ and $R^2$ is independently selected from the group consisting of (a) hydrogen, (b) ($C_1$–$C_4$)alkyl which is unsubstituted or substituted by one of hydroxy-, alkoxy- and alkylthio-, (c) hydroxy, (d) alkoxy, (e) alkylthio, (f) amino and (g) halogen;
each of $R^3$ and $R^4$ is independently selected from the group consisting of (a) hydrogen, (b) ($C_1$–$C_4$)alkyl which is unsubstituted or substituted by one of hydroxy-, alkoxy- and alkylthio-, (c) hydroxy, (d) alkoxy, (e) alkylthio and (f) amino;
Q is selected from the group consisting of —$CO_2H$, —CONR'R", —$SO_3H$, —$SO_2NR'R"$, an activated derivative of —$CO_2H$ and an activated derivative of —$SO_3H$; and
I is NR"'R"" or —NR"'C(O)R"", wherein R', R", R"' and R"" are independently selected from the group consisting of hydrogen, alkyl, an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside and a soluble or non-soluble polymer.

10. A method of transcribing RNA, using a double-stranded DNA as a template, comprising:
(a) hybridizing said double-stranded DNA with a first oligo-nucleic acid analogue and a second oligo-nucleic acid analogue to form a hybrid, each oligo-nucleic acid analogue forming a transcription initiation site with said double-stranded DNA, wherein said first oligo-nucleic acid analogue is hybridized with said double-stranded DNA at a first location thereon and said second oligo-nucleic acid analogue is hybridized with said double-stranded DNA at a second location thereon, said first location being on the same or a different strand of said double-stranded DNA, in relation to said second location;

(b) combining said hybrid with a DNA dependent RNA polymerase and a plurality of nucleoside triphosphates; and (c) thereafter transcribing said RNA by attaching together a plurality of nucleoside triphosphates from step (b), using said double-stranded DNA as a template.

11. The method according to claim 10, wherein said first location is from 0 to 10 base pairs of said double-stranded DNA from said second location.

12. The method according to claim 10, wherein said first location is from 0 to 5 base pairs of said double-stranded DNA from said second location.

13. The method according to claim 9, wherein $2<y+z\leq10$.

14. The method according to claim 9, wherein said at least one oligo-nucleic acid analogue is a compound selected from the group consisting of formula III,

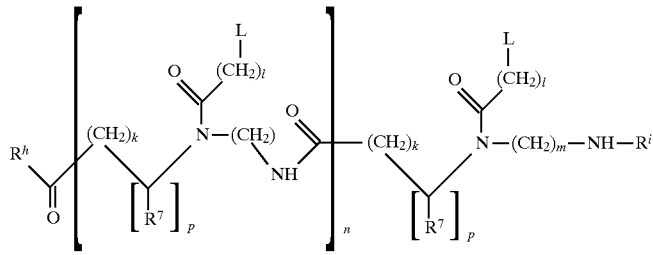

formula IV,

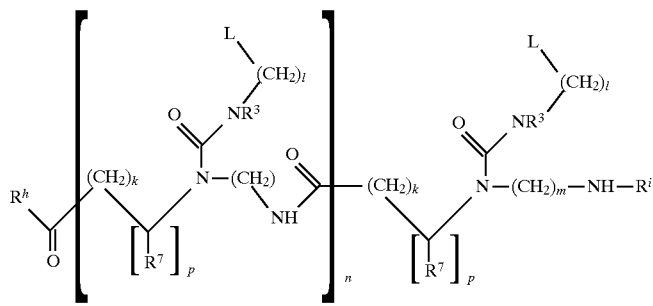

and formula V

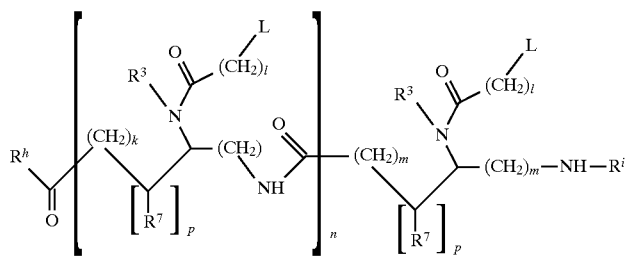

wherein:
each L is independently selected from the group consisting of hydrogen, phenyl, a heterocyclic moiety, at least one naturally occurring nucleobase, and at least one non-naturally occurring nucleobase;

each $R^7$ is independently selected from the group consisting of hydrogen and one of the side chains of naturally occurring alpha amino acids;

n is an integer greater than 1,
each of k, l, and m is, independently, zero or an integer from 1 to 5;
each p is zero or 1;
$R^h$ is one of OH, $NH_2$ and —$NHLysNH_2$; and
$R^i$ is H or $COCH_3$.

15. A method of detecting a double-stranded DNA, comprising:

(a) hybridizing said double-stranded DNA with a least one oligo-nucleic acid analogue to form a hybrid having a transcription initiation site, wherein the hybrid is more stable against heat denaturation than a hybrid between a conventional deoxyribonucleotide corresponding in sequence to said at least one oligo-nucleic acid analogue;

(b) combining said hybrid with a prokaryotic DNA dependent RNA polymerase and a plurality of nucleoside triphosphates;

(c) thereafter transcribing RNA by attaching together a plurality of nucleoside triphosphates from step (b), using said double-stranded DNA as a template; and (d) determining said double-stranded DNA by detecting said RNA produced in step (c).

16. The method according to claim 15, wherein said detecting step (d) comprises hybridizing said RNA with a nucleic acid probe having a sequence which is complementary to said RNA.

17. The method according to claim 15, wherein said at least one oligo-nucleic acid analogue comprises 5 to 60 base pairs.

18. The method according to claim 15, wherein said at least one oligo-nucleic acid analogue comprises 10 to 20 base pairs.

19. The method according to claim 15, wherein said at least one oligo-nucleic acid analogue comprises 17 to 18 base pairs.

20. The method according to claim 15, wherein said at least one oligo-nucleic acid analogue is a peptide nucleic acid.

21. The method according to claim 15, wherein said at least one oligo-nucleic acid analogue comprises a plurality of nucleotide bases attached to a backbone, said backbone comprising a polymer selected from the group consisting of polyaminoethylglycine, polyamide, polythioamide, polysulfinamide and polysulfonamide.

22. The method according to claim 15, wherein said at least one oligo-nucleic acid analogue comprises a polyamide backbone and a plurality of ligands, each of said plurality of ligands being bonded directly or indirectly to an aza nitrogen atom in said polyamide backbone, wherein each ligand-binding aza nitrogen atom is separated from an adjacent ligand-binding aza nitrogen atom by from 4 to 8 intervening atoms in said polyamide backbone.

23. The method according to claim 15, wherein said at least one oligo-nucleic acid analogue hybridizes with one strand of said double-stranded DNA having a sequence which is complementary to said at least one oligo-nucleic acid analogue, thereby displacing the other strand of said double-stranded DNA from said one strand of said double-stranded DNA.

24. The method according to claim 15, wherein said at least one oligo-nucleic acid analogue is a compound of formula 1:

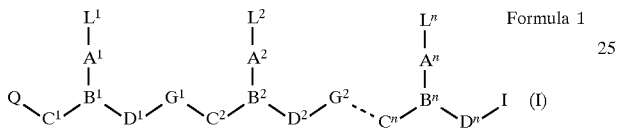

Formula 1 wherein:
n is at least 2,
each of $L^1$–$L^n$ is independently selected from the group consisting of hydrogen, hydroxy, ($C_1$–$C_4$)alkanoyl, a naturally occurring nucleobase, a non-naturally occurring nucleobase, an aromatic moiety, a DNA intercalator, a nucleobase-binding group, a heterocyclic moiety, and a reporter ligand;
each of $C^1$–$C^n$ is independently selected from the group consisting of $(CR^6R^7)_y$, $(CHR^6CHR^7)_y$ and $(CR^6R^7CH_2)_y$,
wherein $R^6$ is hydrogen and $R^7$ is selected from the group consisting of one of the side chains of naturally occurring alpha amino acids, or
$R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, wherein $R^3$ and $R^4$ are as defined below, and wherein $R^5$ is selected from the group consisting of hydrogen, ($C_1$–$C_6$)alkyl, hydroxy, alkoxy and alkylthio-substituted ($C_1$–$C_6$) alkyl, or
$R^6$ and $R^7$, taken together, form an alicyclic or heterocyclic system;
each of $D^1$–$D^n$ is independently selected from the group consisting of $(CR^6R^7)_z$, $(CH_2CR^6R^7)_z$ and $(CHR^6CHR^7)_z$
wherein $R^6$ and $R^7$ are as defined above;
each of y and z is zero or an integer from 1 to 10, y+z being at least 2;
each of $G^1$–$G^{n-1}$ is independently selected from the group consisting of —$NR^3CO$—, —$CONR^3$—, —$NR^3CS$—, —$CSNR^3$—, —$NR^3SO$—, —$SONR^3$—, —$NR^3SO_2$— and —$SO_2NR^3$—, where $R^3$ is as defined below;
each of $A^1$–$A^n$ and $B^1$–$B^n$ are selected such that:

(a) A is selected from the group consisting of a group of formula (IIa), (IIb), (IIc) and (IId), and B is N or $R^3N^+$, or
(b) A is a group of formula (IId) and B is CH;

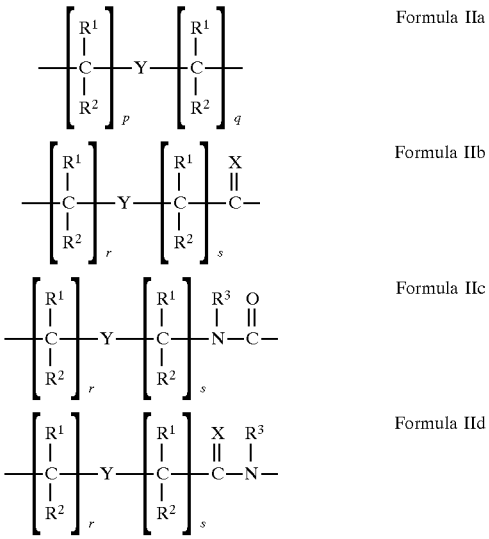

wherein:
X is selected from the group consisting of O, S, Se, $NR^3$, $CH_2$ and $C(CH_3)_2$;
Y is selected from the group consisting of a single bond, O, S and $NR^4$;
each of p and q is zero or an integer from 1 to 5;
each of r and s is zero or an integer from 1 to 5;
each of $R^1$ and $R^2$ is independently selected from the group consisting of (a) hydrogen, (b) ($C^1$–$C_4$)alkyl which is unsubstituted or substituted by one of hydroxy-, alkoxy- and alkylthio-, (c) hydroxy, (d) alkoxy, (e) alkylthio, (f) amino and (g) halogen;
each of $R^3$ and $R^4$ is independently selected from the group consisting of (a) hydrogen, (b) ($C_1$–$C_4$)alkyl which is unsubstituted or substituted by one of hydroxy-, alkoxy- and alkylthio-, (c) hydroxy, (d) alkoxy, (e) alkylthio and (f) amino;
Q is selected from the group consisting of —$CO_2H$, —CONR'R", —$SO_3H$, —$SO_2NR'R"$, an activated derivative of —$CO_2H$ and an activated derivative of —$SO_3H$; and
I is NR'''R" or —NR''' C(O)R"", wherein R', R", R''' and R"" are independently selected from the group consisting of hydrogen, alkyl, an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside and a soluble or non-soluble polymer.

25. The method according to claim 16, wherein said nucleic acid probe comprises a detectable label.

26. The method according to claim 24, wherein 2<y+z ≦10.

27. The method according to claim 24, wherein said at least one oligo-nucleic acid analogue is a compound selected from the group consisting of formula III,

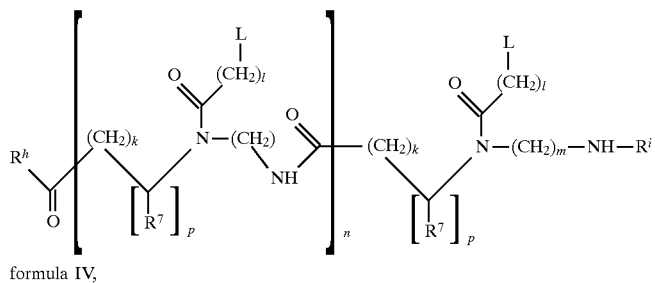

Formula III

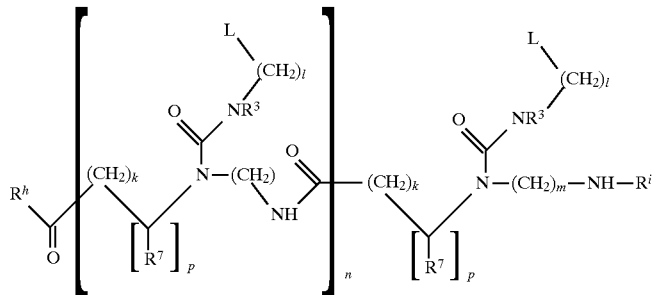

Formula IV

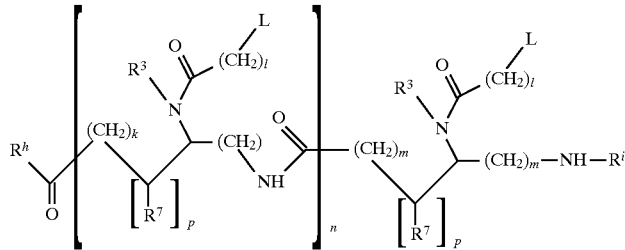

Formula V wherein:
each L is independently selected from the group consisting of hydrogen, phenyl, a heterocyclic moiety, at least one naturally occurring nucleobase, and at least one non-naturally occurring nucleobase;
each $R^7$ is independently selected from the group consisting of hydrogen and one of the side chains of naturally occurring alpha amino acids;
n is an integer greater than 1,
each of k, l, and m is, independently, zero or an integer from 1 to 5;
each p is zero or 1;
$R^h$ is one of OH, $NH_2$ and —$NHLysNH_2$; and
$R^i$ is H or $COCH_3$.

28. A method of amplifying RNA, comprising:
(a) hybridizing a double-stranded DNA with at least one oligo-nucleic acid analogue forming a transcription initiation site with said double-stranded DNA, to form a hybrid;
(b) combining said hybrid formed in step (a) with a DNA dependent RNA polymerase and a plurality of nucleoside triphosphates;
(c) thereafter transcribing RNA by attaching together a plurality of nucleoside triphosphates from step (b), using said double-stranded DNA as a template;
(d) hybridizing said RNA produced in step (c) with a nucleic acid primer, to form a hybrid;
(e) extending said nucleic acid primer of said hybrid formed in step (d), using said RNA as a template, to produce an extension product; and
(f) transcribing RNA, using the extension product produced in step (e) as a template.

29. The method according to claim 28, wherein said at least one oligo-nucleic acid analogue comprises 5 to 60 base pairs.

30. The method according to claim 28, wherein said at least one oligo-nucleic acid analogue comprises 10 to 20 base pairs.

31. The method according to claim 28, wherein said at least one oligo-nucleic acid analogue comprises 17 to 18 base pairs.

32. The method according to claim 28, wherein said at least one oligo-nucleic acid analogue is a peptide nucleic acid.

33. The method according to claim 28, wherein said at least one oligo-nucleic acid analogue comprises a plurality of nucleotide bases attached to a backbone, said backbone comprising a polymer selected from the group consisting of polyaminoethylglycine, polyamide, polythioamide, polysulfinamide and polysulfonamide.

34. The method according to claim 28, wherein said at least one oligo-nucleic acid analogue comprises a polyamide backbone and a plurality of ligands, each of said plurality of ligands being bonded directly or indirectly to an aza nitrogen atom in said polyamide backbone, wherein each ligand-binding aza nitrogen atom is separated from an adjacent ligand-binding aza nitrogen atom by from 4 to 8 intervening atoms in said polyamide backbone.

35. The method according to claim 28, wherein, in step (a), said at least one oligo-nucleic acid analogue hybridizes with one strand of said double-stranded DNA having a sequence which is complementary to said at least one oligo-nucleic acid analogue, thereby displacing the other strand of said double-stranded DNA from said one strand of said double-stranded DNA.

36. The method according to claim 28, wherein said at least one oligo-nucleic acid analogue is a compound of formula 1:

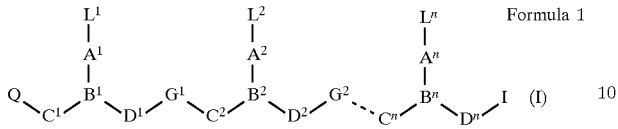
Formula 1 wherein:

n is at least 2, each of $L^1$–$L^n$ is independently selected from the group consisting of hydrogen, hydroxy, $(C_1$–$C_4)$alkanoyl, a naturally occurring nucleobase, a non-naturally occurring nucleobase, an aromatic moiety, a DNA intercalator, a nucleobase-binding group, a heterocyclic moiety, and a reporter ligand;

each of $C^1$–$C^n$ is independently selected from the group consisting of $(CR^6R^7)_y$, $(CHR^6CHR^7)_y$ and $(CR^6R^7CH_2)_y$ wherein $R^6$ is hydrogen and $R^7$ is selected from the group consisting of one of the side chains of naturally occurring alpha amino acids, or $R^6$ and $R^7$ are independently selected from the group consisting of hydrogen, $(C_2$–$C_6)$alkyl, aryl, aralkyl, heteroaryl, hydroxy, $(C_1$–$C_6)$alkoxy, $(C_1$–$C_6)$ alkylthio, $NR^3R^4$ and $SR^5$, wherein $R^3$ and $R^4$ are as defined below, and wherein $R^5$ is selected from the group consisting of hydrogen, $(C_1$–$C_6)$alkyl, hydroxy, alkoxy and alkylthio-substituted $(C_1$–$C_6)$ alkyl, or $R^6$ and $R^7$, taken together, form an alicyclic or heterocyclic system;

each of $D^1$–$D^n$ is independently selected from the group consisting of $(CR^6R^7)_z$, $(CH_2CR^6R^7)_z$ and $(CHR^6CHR^7)_z$ wherein $R^6$ and $R^7$ are as defined above;

each of y and z is zero or an integer from 1 to 10, y+z being at least 2;

each of $G^1$–$G^{n-1}$ is independently selected from the group consisting of —$NR^3CO$—, —$CONR^3$—, —$NR^3CS$—, —$CSNR^3$—, —$NR^3SO$—, —$SONR^3$—, —$NR^3SO_2$— and —$SO_2NR^3$—, where $R^3$ is as defined below;

each of $A^1$–$A^n$ and $B^1$–$B^n$ are selected such that:

(a) A is selected from the group consisting of a group of formula (IIa), (IIb), (IIc) and (IId), and B is N or $R^3N^+$, or (b) A is a group of formula (IId) and B is CH;

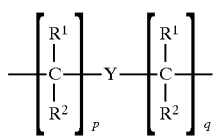
Formula IIa

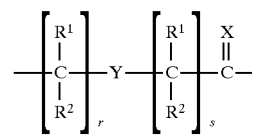
Formula IIb

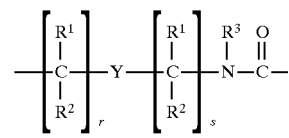
Formula IIc

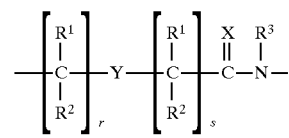
Formula IId

X is selected from the group consisting of O, S, Se, $NR^3$, $CH_2$ and $C(CH_3)_2$;

Y is selected from the group consisting of a single bond, O, S and $NR_4$;

each of p and q is zero or an integer from 1 to 5;

each of r and s is zero or an integer from 1 to 5;

each of $R^1$ and $R^2$ is independently selected from the group consisting of (a) hydrogen, (b) $(C_1$–$C_4)$alkyl which is unsubstituted or substituted by one of hydroxy-, alkoxy- and alkylthio-, (c) hydroxy, (d) alkoxy, (e) alkylthio, (f) amino and (g) halogen;

each of $R^3$ and $R^4$ is independently selected from the group consisting of (a) hydrogen, (b) $(C_1$–$C_4)$alkyl which is unsubstituted or substituted by one of hydroxy-, alkoxy- and alkylthio-, (c) hydroxy, (d) alkoxy, (e) alkylthio and (f) amino;

Q is selected from the group consisting of —$CO_2H$, —$CONR'R''$, —$SO_3H$, —$SO_2NR'R''$, an activated derivative of —$CO_2H$ and an activated derivative of —$SO_3H$; and I is NR'''R'''' or —NR'''C(O)R'''', wherein R', R'', R''' and R'''' are independently selected from the group consisting of hydrogen, alkyl, an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside and a soluble or non-soluble polymer.

37. The method according to claim 36, wherein 2<y+z≦10.

38. The method according to claim 36, wherein said at least one oligo-nucleic acid analogue is a compound selected from the group consisting of formula III,

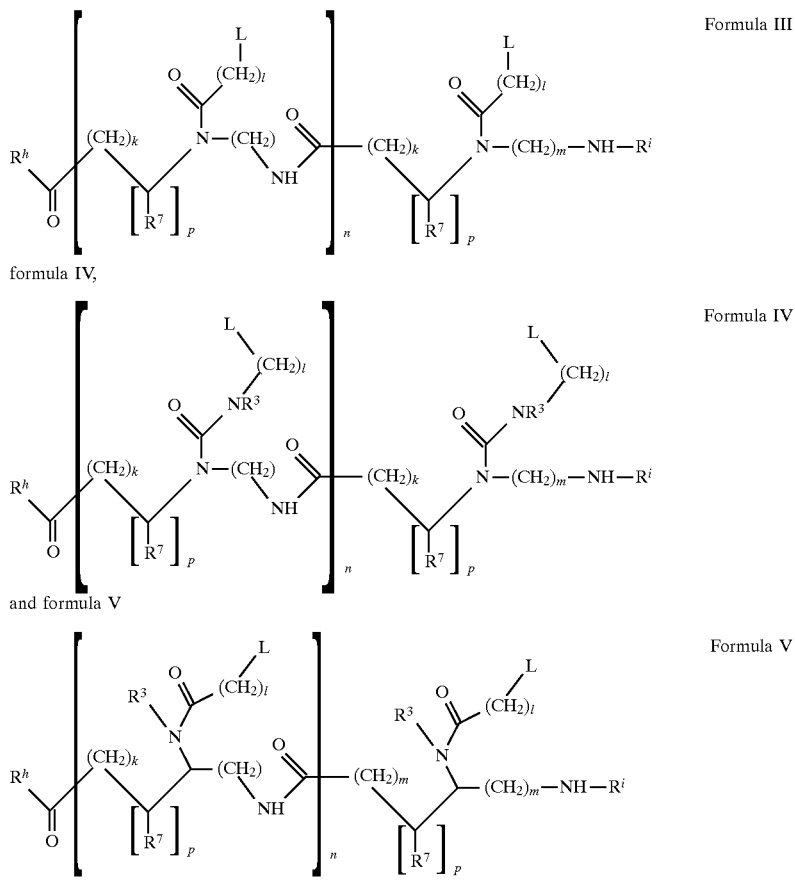

formula IV, and formula V

Formula III

Formula IV

Formula V wherein
each L is independently selected from the group consisting of hydrogen, phenyl, a heterocyclic moiety, at least one naturally occurring nucleobase, and at least one non-naturally occurring nucleobase;
each $R^7$ is independently selected from the group consisting of hydrogen and one of the side chains of naturally occurring alpha amino acids;
n is an integer greater than 1,
each of k, l, and m is, independently, zero or an integer from 1 to 5;
each p is zero or 1;
$R^h$ is one of OH, $NH_2$ and —$NHLysNH_2$; and
$R^i$ is H or $COCH_3$.

39. A method of converting a starting nucleic acid into a double-stranded DNA template for transcribing RNA, comprising:
(a) hybridizing said starting nucleic acid with first DNA oligonucleotide comprising a specific binding sequence, to form a first hybrid;
(b) extending said DNA oligonucleotide of said first hybrid, using said starting nucleic acid as a template, to form a first extension hybrid comprising said starting nucleic acid and a first extension product;
(c) denaturing said first extension hybrid formed in (b);
(d) hybridizing said first extension product with a second DNA oligonucleotide comprising a sequence which is complementary to a portion of said first extension product;
(e) extending said second DNA oligonucleotide using said first extension product as a template to form a second extension hybrid comprising said first extension product and said second extension product;

(f) thereafter hybridizing said second extension hybrid with an oligo-nucleic acid analogue comprising a sequence which is complementary to said specific binding sequence, to form a double-stranded DNA template for transcribing RNA.

40. The method according to claim 39, wherein said starting nucleic acid is RNA.
41. The method according to claim 39, wherein said starting nucleic acid is DNA.
42. The method according to claim 39, wherein said first DNA oligonucleotide further comprises a nucleic acid sequence S1 which hybridizes with said starting nucleic acid toward the 3'-end of said starting nucleic acid.
43. The method according to claim 39, wherein said specific binding sequence comprises more than 8 nucleotides.
44. The method according to claim 39, wherein said specific binding sequence consists of a plurality of pyrimidine bases.
45. The method according to claim 39, wherein said oligo-nucleic acid analogue comprises 5 to 60 base pairs.
46. The method according to claim 39, wherein said oligo-nucleic acid analogue comprises 10 to 20 base pairs.
47. The method according to claim 39, wherein said oligo-nucleic acid analogue comprises 17 to 18 base pairs.
48. The method according to claim 39, wherein said oligo-nucleic acid analogue is a peptide nucleic acid.
49. The method according to claim 39, wherein said oligo-nucleic acid analogue comprises a plurality of nucleotide bases attached to a backbone, said backbone comprising a polymer selected from the group consisting of polyaminoethylglycine, polyamide, polythioamide, polysulfinamide and polysulfonamide.
50. The method according to claim 39, wherein said oligo-nucleic acid analogue comprises a polyamide backbone and a plurality of ligands, each of said plurality of ligands being bonded directly or indirectly to an aza nitrogen atom in said polyamide backbone, wherein each ligand-binding aza nitrogen atom is separated from an adjacent ligand-binding aza nitrogen atom by from 4 to 8 intervening atoms in said polyamide backbone.

51. The method according to claim 39, wherein said oligo-nucleic acid analogue is a compound of formula 1:

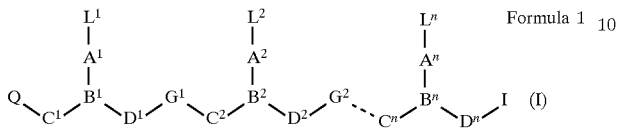

wherein:

n is at least 2, each of $L^1$–$L^n$ is independently selected from the group consisting of hydrogen, hydroxy, ($C_1$–$C_4$)alkanoyl, a naturally occurring nucleobase, a non-naturally occurring nucleobase, an aromatic moiety, a DNA intercalator, a nucleobase-binding group, a heterocyclic moiety, and a reporter ligand;

each of $C^1$–$C^n$ is independently selected from the group consisting of $(CR^6R^7)_y$, $(CHR^6CHR^7)_y$ and $(CR^6R^7CH_2)_y$, wherein $R^6$ is hydrogen and $R^7$ is selected from the group consisting of one of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$) alkylthio, $NR^3R^4$ and $SR^5$, wherein $R^3$ and $R^4$ are as defined below, and wherein $R^5$ is selected from the group consisting of hydrogen, ($C_1$–$C_6$)alkyl, hydroxy, alkoxy and alkylthio-substituted ($C_1$–$C_6$) alkyl, or $R^6$ and $R^7$, taken together, form an alicyclic or heterocyclic system;

each of $D^1$–$D^n$ is independently selected from the group consisting of $(CR^6R^7)_z$, $(CH_2CR^6R^7)_z$ and $(CHR^6CHR^7)_z$ wherein $R^6$ and $R^7$ are as defined above;

each of y and z is zero or an integer from 1 to 10, y+z being at least 2;

each of $G^1G^{n-1}$ is independently selected from the group consisting of —$NR^3CO$—, —$CONR^3$—, —$NR^3CS$—, —$CSNR^3$—, —$NR^3SO$—, —$SONR^3$—, —$NR^3SO_2$— and —$SO_2NR^3$—, where $R^3$ is as defined below;

each of $A^1$–$A^n$ and $B^1$–$B^n$ are selected such that:

(a) A is selected from the group consisting of a group of formula (IIa), (IIb), (IIc) and (IId), and B is N or $R^3N^+$, or (b) A is a group of formula (IId) and B is CH;

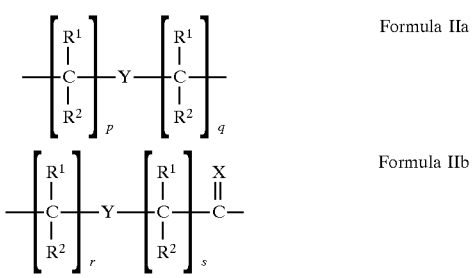

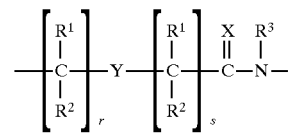

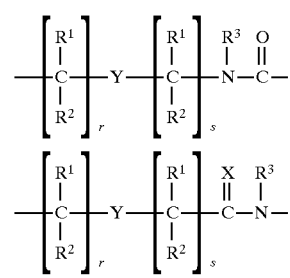

wherein:

X is selected from the group consisting of O, S, Se, $NR^3$, $CH_2$ and $C(CH_3)_2$;

Y is selected from the group consisting of a single bond, O, S and $NR_4$;

each of p and q is zero or an integer from 1 to 5;

each of r and s is zero or an integer from 1 to 5;

each of $R^1$ and $R^2$ is independently selected from the group consisting of (a) hydrogen, (b) ($C_1$–$C_4$)alkyl which is unsubstituted or substituted by one of hydroxy-, alkoxy- and alkylthio-, (c) hydroxy, (d) alkoxy, (e) alkylthio, (f) amino and (g) halogen;

each of $R^3$ and $R^4$ is independently selected from the group consisting of (a) hydrogen, (b) ($C_1$–$C_4$)alkyl which is unsubstituted or substituted by one of hydroxy-, alkoxy- and alkylthio-, (c) hydroxy, (d) alkoxy, (e) alkylthio and (f) amino;

Q is selected from the group consisting of —$CO_2H$, —CONR'R'', —$SO_3H$, —$SO_2NR'R''$, an activated derivative of —$CO_2H$ and an activated derivative of —$SO_3H$; and I is NR'''R'''' or —NR'''C(O)R'''', wherein R', R'', R''' and R'''' are independently selected from the group consisting of hydrogen, alkyl, an amino protecting group, a reporter ligand, an intercalator, a chelator, a peptide, a protein, a carbohydrate, a lipid, a steroid, a nucleoside, a nucleotide, a nucleotide diphosphate, a nucleotide triphosphate, an oligonucleotide, an oligonucleoside and a soluble or non-soluble polymer.

52. The method according to claim 42, wherein said nucleic acid sequence S1 comprises at least 15 nucleotides.

53. The method according to claim 42, wherein said nucleic acid sequence S1 comprises about 20 nucleotides.

54. The method according to claim 42, wherein said first DNA oligonucleotide further comprises a nucleic acid sequence S2 which hybridizes with said starting nucleic acid further upstream toward the 5'-end of said starting nucleic acid, compared to said nucleic acid sequence S1, wherein said specific binding sequence is located between said nucleic acid sequence S1 and said nucleic acid sequence S2.

55. The method according to claim 54, wherein said nucleic acid sequence S2 comprises more than 15 nucleotides.

56. The method according to claim 54, wherein said nucleic acid sequence S2 comprises about 40 nucleotides.

57. The method according to claim 43, wherein said specific binding sequence comprises about 10 nucleotides.

58. The method according to claim 51, wherein 2<y+z≦10.

59. The method according to claim 51, wherein said at least one oligo-nucleic acid analogue is a compound selected from the group consisting of formula III,

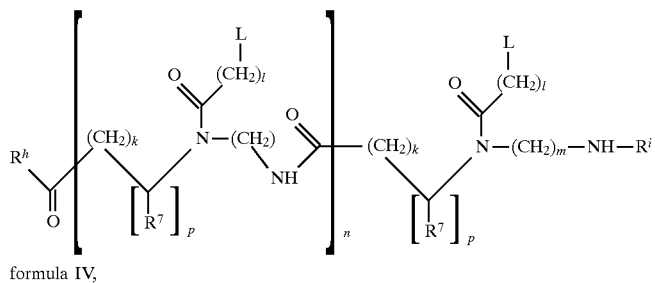

Formula III

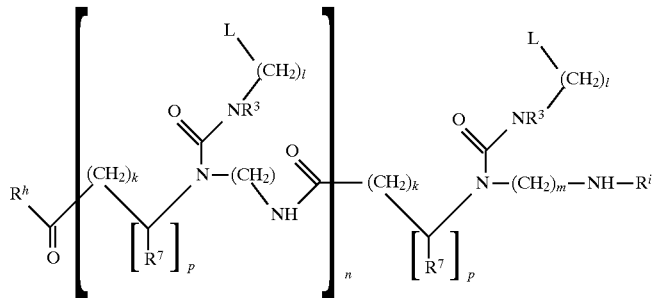

Formula IV

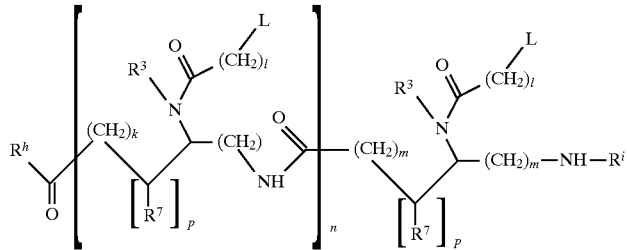

Formula V wherein
- each L is independently selected from the group consisting of hydrogen, phenyl, a heterocyclic moiety, at least one naturally occurring nucleobase, and at least one non-naturally occurring nucleobase;
- each $R^7$ is independently selected from the group consisting of hydrogen and one of the side chains of naturally occurring alpha amino acids;
- n is an integer greater than 1,
- each of k, l, and m is, independently, zero or an integer from 1 to 5;
- each p is zero or 1;
- $R^h$ is one of OH, $NH_2$ and —$NHLysNH_2$; and
- $R^i$ is H or $COCH_3$.

* * * * *